United States Patent
Swedlow et al.

(10) Patent No.: US 8,090,425 B2
(45) Date of Patent: *Jan. 3, 2012

(54) OXIMETER SENSOR WITH DIGITAL MEMORY ENCODING PATIENT DATA

(75) Inventors: David Swedlow, Danville, CA (US); Michael E. Fein, Mountain View, CA (US); Marcia Fein, legal representative, Mountain View, CA (US); Paul D. Mannheimer, Danville, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 1822 days.

This patent is subject to a terminal disclaimer.

(21) Appl. No.: 11/239,817

(22) Filed: Sep. 30, 2005

(65) Prior Publication Data

US 2006/0025660 A1 Feb. 2, 2006

Related U.S. Application Data

(63) Continuation of application No. 10/452,806, filed on May 30, 2003, which is a continuation of application No. 09/943,899, filed on Aug. 30, 2001, now Pat. No. 6,606,510.

(60) Provisional application No. 60/229,616, filed on Aug. 31, 2000.

(51) Int. Cl.
*A61B 5/1455* (2006.01)

(52) U.S. Cl. .................................. 600/323

(58) Field of Classification Search ............ 600/323
See application file for complete search history.

(56) References Cited

U.S. PATENT DOCUMENTS

| | | |
|---|---|---|
| 3,720,199 A | 3/1973 | Rishton et al. |
| 3,790,910 A | 2/1974 | McCormack |
| 3,797,479 A | 3/1974 | Graham |
| 4,041,935 A | 8/1977 | Garbe |
| 4,210,155 A | 7/1980 | Grimes |
| 4,303,984 A | 12/1981 | Houvig |
| 4,446,715 A | 5/1984 | Bailey |
| 4,621,643 A | 11/1986 | New, Jr. et al. |
| 4,653,498 A * | 3/1987 | New et al. ............ 600/324 |
| 4,684,245 A | 8/1987 | Goldring |
| 4,684,246 A | 8/1987 | Downing |
| 4,700,708 A | 10/1987 | New, Jr. et al. |
| 4,714,080 A | 12/1987 | Edgar et al. |
| 4,717,080 A | 1/1988 | Sauer |
| 4,734,873 A | 3/1988 | Malloy et al. |
| 4,845,649 A | 7/1989 | Eckardt et al. |
| 4,845,873 A | 7/1989 | Hazlett |
| 4,858,615 A | 8/1989 | Meinema |
| 4,862,872 A | 9/1989 | Yabe et al. |
| 4,913,150 A | 4/1990 | Cheung |

(Continued)

FOREIGN PATENT DOCUMENTS

DE 3028061 9/1982

(Continued)

*Primary Examiner* — Eric Winakur
(74) *Attorney, Agent, or Firm* — Fletcher Yoder

(57) ABSTRACT

The present invention provides a memory chip for use in an oximeter sensor, or an associated adapter or connector circuit. The memory chip allows the storing of patient related data, such as patient trending data or a patient ID, to provide enhanced capabilities for the oximeter sensor. In addition to providing unique data to store in such a memory, the present invention include unique uses of the data stored in such a memory.

7 Claims, 1 Drawing Sheet

U.S. PATENT DOCUMENTS

| | | | |
|---|---|---|---|
| 4,942,877 A | 7/1990 | Sakai et al. | |
| 5,007,423 A | 4/1991 | Branstetter | |
| 5,008,843 A | 4/1991 | Poelsler et al. | |
| 5,016,198 A | 5/1991 | Schreiber | |
| 5,025,791 A | 6/1991 | Niwa | |
| 5,058,588 A | 10/1991 | Kaestle | |
| 5,070,732 A | 12/1991 | Duncan et al. | |
| 5,162,725 A | 11/1992 | Hodson et al. | |
| 5,226,417 A | 7/1993 | Swedlow et al. | |
| 5,246,003 A | 9/1993 | DeLonzor | |
| 5,259,381 A | 11/1993 | Cheung et al. | |
| 5,329,931 A * | 7/1994 | Clauson et al. | 600/323 |
| 5,341,291 A | 8/1994 | Roizen et al. | |
| 5,347,476 A | 9/1994 | McBean, Sr. | |
| 5,360,005 A * | 11/1994 | Wilk | 600/437 |
| 5,365,462 A | 11/1994 | McBean, Sr. | |
| 5,368,026 A | 11/1994 | Swedlow et al. | |
| 5,371,128 A | 12/1994 | Ulman et al. | |
| 5,372,141 A | 12/1994 | Gallup et al. | |
| 5,385,144 A | 1/1995 | Yamanishi et al. | |
| 5,425,375 A | 6/1995 | Chin | |
| 5,429,129 A | 7/1995 | Lovejoy et al. | |
| 5,431,170 A | 7/1995 | Mathews | |
| 5,443,801 A | 8/1995 | Langford | |
| 5,448,991 A | 9/1995 | Polson et al. | |
| 5,513,646 A | 5/1996 | Lehrman et al. | |
| 5,528,519 A | 6/1996 | Ohkura et al. | |
| 5,627,531 A | 5/1997 | Posso et al. | |
| 5,645,059 A | 7/1997 | Fein et al. | |
| 5,645,060 A | 7/1997 | Yorkey | |
| 5,645,069 A | 7/1997 | Lee | |
| 5,660,163 A | 8/1997 | Schulman et al. | |
| 5,660,176 A | 8/1997 | Iliff | |
| 5,678,448 A | 10/1997 | Fullen et al. | |
| 5,682,877 A | 11/1997 | Mondry | |
| 5,718,235 A | 2/1998 | Golosarsky et al. | |
| 5,720,293 A | 2/1998 | Quinn et al. | |
| 5,730,124 A | 3/1998 | Yamauchi | |
| 5,758,644 A | 6/1998 | Diab | |
| 5,800,350 A | 9/1998 | Coppleson et al. | |
| 5,818,583 A | 10/1998 | Sevick-Muraca et al. | |
| 5,830,121 A | 11/1998 | Enomoto et al. | |
| 5,830,135 A | 11/1998 | Bosque | |
| 5,855,609 A | 1/1999 | Knapp | |
| 5,865,736 A * | 2/1999 | Baker et al. | 600/323 |
| 5,954,644 A * | 9/1999 | Dettling et al. | 600/322 |
| 5,961,446 A | 10/1999 | Beller | |
| 5,964,701 A | 10/1999 | Asada et al. | |
| 5,987,343 A | 11/1999 | Kinast | |
| 5,995,859 A | 11/1999 | Takahashi | |
| 6,004,276 A | 12/1999 | Wright et al. | |
| 6,018,673 A | 1/2000 | Chin et al. | |
| 6,023,541 A | 2/2000 | Merchant et al. | |
| 6,044,283 A | 3/2000 | Fein et al. | |
| 6,095,984 A | 8/2000 | Amano et al. | |
| 6,104,938 A | 8/2000 | Huiku et al. | |
| 6,122,536 A | 9/2000 | Sun et al. | |
| 6,241,679 B1 | 6/2001 | Curran | |
| 6,298,252 B1 | 10/2001 | Kovach et al. | |
| 6,298,255 B1 | 10/2001 | Cordero | |
| 6,308,089 B1 | 10/2001 | von der Ruhr et al. | |
| 6,356,774 B1 | 3/2002 | Bernstein et al. | |
| 6,360,114 B1 | 3/2002 | Diab et al. | |
| 6,374,129 B1 | 4/2002 | Chin et al. | |
| 6,377,829 B1 | 4/2002 | Al-Ali | |
| 6,405,087 B1 | 6/2002 | Snell | |
| 6,463,310 B1 | 10/2002 | Swedlow et al. | |
| 6,466,808 B1 | 10/2002 | Chin | |
| 6,591,123 B2 | 7/2003 | Fein | |
| 6,608,934 B2 | 8/2003 | Scheirer et al. | |
| 6,708,049 B1 | 3/2004 | Berson et al. | |
| 6,801,797 B2 | 10/2004 | Mannheimer et al. | |
| 6,845,256 B2 | 1/2005 | Chin et al. | |
| 6,934,571 B2 | 8/2005 | Wiesmann et al. | |
| 6,950,687 B2 | 9/2005 | Al-Ali | |
| 6,979,812 B2 | 12/2005 | Al-Ali | |
| 6,988,056 B2 | 1/2006 | Cook | |
| 7,048,687 B1 | 5/2006 | Reuss et al. | |
| 7,187,441 B1 | 3/2007 | Sevick-Muraca et al. | |
| 7,260,425 B2 | 8/2007 | Chin et al. | |
| 7,272,425 B2 | 9/2007 | Al-Ali | |
| 7,457,652 B2 | 11/2008 | Porges et al. | |
| 2002/0103423 A1 | 8/2002 | Chin et al. | |
| 2003/0135099 A1 | 7/2003 | Al-Ali | |
| 2005/0070773 A1 | 3/2005 | Chin et al. | |
| 2005/0070775 A1 | 3/2005 | Chin et al. | |
| 2005/0165323 A1 | 7/2005 | Montgomery et al. | |
| 2006/0030763 A1 | 2/2006 | Mannheimer et al. | |
| 2006/0030764 A1 | 2/2006 | Porges et al. | |
| 2006/0161054 A1 | 7/2006 | Reuss et al. | |
| 2006/0224059 A1 | 10/2006 | Swedlow et al. | |
| 2006/0259925 A1 | 11/2006 | Lemmons et al. | |
| 2007/0156034 A1 | 7/2007 | Al-Ali | |
| 2007/0208235 A1 | 9/2007 | Besson et al. | |
| 2007/0299328 A1 | 12/2007 | Chin et al. | |
| 2008/0287757 A1 | 11/2008 | Berson et al. | |

FOREIGN PATENT DOCUMENTS

| | | |
|---|---|---|
| EP | 0 949 506 A2 | 10/1999 |
| GB | 2247838 | 3/1992 |
| JP | 3939782 B2 | 7/2007 |
| JP | 4038280 B2 | 1/2008 |
| WO | WO 89/09023 | 10/1989 |
| WO | WO 93/06775 | 4/1993 |
| WO | WO 93/06776 | 4/1993 |
| WO | WO 93/06778 | 4/1993 |
| WO | WO 97/29678 | 8/1997 |
| WO | WO 97/47233 | 12/1997 |

* cited by examiner

OXIMETER SENSOR WITH DIGITAL MEMORY ENCODING PATIENT DATA

CROSS-REFERENCE TO RELATED APPLICATIONS

This application is a Continuation of U.S. application Ser. No. 10/452,806, filed May 30, 2003, which is a continuation of U.S. application Ser. No. 09/943,899, filed Aug. 30, 2001, now U.S. Pat. No. 6,606,510, which claims priority to U.S. Provisional Application Ser. No. 60/229,616, filed Aug. 31, 2000, all the disclosures of which are hereby incorporated by reference.

BACKGROUND OF THE INVENTION

The present invention relates to oximetry sensors and, in particular, pulse oximetry sensors which include coded information relating to patients.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

An encoding mechanism is shown in U.S. Pat. No. 4,700,708, the disclosure of which is incorporated herein by reference. This mechanism relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary, a coding resistor is placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe.

U.S. Pat. No. 5,259,381 recognizes that the coded value of the wavelength of the red LED provided by a coding resistor may be inaccurate, since the actual wavelength can vary with temperature. Accordingly, this patent teaches including a temperature sensor in the oximeter probe to measure the actual temperature. With the actual temperature, and the coded wavelength value, a look-up table can be consulted to determine the actual LED wavelength for that temperature.

Another method of storing coded information regarding the characteristics of the LEDs is shown in U.S. Pat. No. 4,942,877 assigned to Minolta. This patent discloses using an EPROM memory to store digital information, which can be provided in parallel or serially from the sensor probe to the remote oximeter. The memory is described as storing coefficients for the saturation equation, wavelength subwavelength (where 2 peaks for LED), half-width of wavelength spectrum emitted by LED, intensity of LEDS or ratio, and on time of LEDS (written by the processor).

Other examples of coding probe characteristics exist in other areas. Multiple calibration values are sometimes required, with this making the circuitry more complex or requiring many leads. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another probe with digital characterization information stored in a PROM, which is read serially using a shift register.

Typically, the coding element is mounted in the probe itself. For instance, U.S. Pat. No. 4,621,643 shows the coding resistor mounted in the probe element itself. In addition, U.S. Pat. No. 5,246,003 shows the coding resistor being formed with a printed conductive material on the probe itself.

In some devices, an electrical connector coupled by a cable to a device attached to a patient may include a coding element. For example, U.S. Pat. No. 3,720,199 shows an intra-aortic balloon catheter with a connector between the catheter and a console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

U.S. Pat. No. 5,645,059 teaches using a modulated signal to provide the coded data to a remote analyzer. U.S. Pat. No. 5,429,129 shows using a voltage regulator to produce a specific voltage value in response to an attempt to read by the analyzer.

Hewlett-Packard Company U.S. Pat. No. 5,058,588 teaches an oximeter sensor with an encoding element that could be resistor, ROM, or customized integrated circuit. The encoding element encodes the type of sensor (in particular, type indicating area of placement on body—finger, ear, foot, arm; also, the type of sensor can indicate transmission/reflection type, or adult/neonate {indicating correction to be performed on-theoretical oxygen-saturation, allow switching between physiological limits such as minimum/maximum pulse rates for adults/neonates}; the maximum driving current may be adapted according to type of sensor, and contact of sensor with tissue can be tested by means of an attenuation measurement if sensor type is known).

Nellcor U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

A number of catheter patents also discuss encoding information in the catheter. Sentron U.S. Pat. No. 4,858,615 teaches encoding the type of sensor, type number, serial number, date of production, safe use life of the sensor, correction data for non-linearity, pressure sensitivity, offset, and temperature sensitivity.

Interflo Medical Published PCT Application No. PCT/US92/08263, Publication No. WO 93/06776 teaches encoding patient specific data, size, manufacture date, batch number, sterilization date, expiration date, transducer number and type, manufacturer's name and address, thermistor heating element resistance, filament efficiency, program segments or patient historical data, format version for the calibration data, trademark information, catheter unique serial number, ship date, other date and time information, security code to identify manufacturer, thermal mass, filament composition, coefficient of resistance, layout byte, checksum, copyright, number of seconds since a certain date, patient weight, patient height, timestamp of 1st CO data point, and a count of all CO data points in EEPROM.

Dulex-Ohmeda of Boulder, Colo. markets an oximeter sensor product that encodes data into resistor values representing pointers to a lookup table containing coefficients (as in U.S. Pat. No. 4,700,708) as well as indicating a range of LED drive current to use with the sensor. The LEDs are driven with a higher or lower drive currents depending upon the value of the resistor in a particular sensor.

Honeywell U.S. Pat. No. 4,303,984 (expires Dec. 14, 1999) describes a memory which stores characterization information, such as linearization information for a pressure sensor. Alnor Instrument U.S. Pat. No. 5,162,725 describes storing both calibration and ID information in a sensor memory. Seimans U.S. Pat. No. 5,016,198 describes a coding memory in a sensor with data for defining sensor's characteristic curve. McBean U.S. Pat. No. 5,365,462 describes a date code in a sensor memory. Honeywell U.S. Pat. No. 4,734,873 describes a pressure sensor with a PROM storing coefficients for a polynomial. Robert Bosch U.S. Pat. No. 4,845,649 describes a PROM in a sensor storing correcting data.

McBean U.S. Pat. No. 5,371,128 relates to EEPROM in sensor with sensor type code and calibration data. McBean U.S. Pat. No. 5,347,476 describes an accuracy code. Otax U.S. Pat. No. 5,528,519 shows a PROM in a connector for oximeter.

Square D Company U.S. Pat. No. 5,070,732 shows calibration data in a sensor memory. Baxter U.S. Pat. No. 5,720,293 talks about different calibration information for a catheter, including a security code (encryption is discussed), serial number, model number, ID data such as calibration, manufacture, sterilization and ship date or other date and time information, a software program segment, security code for identifying whether sensor made by same manufacturer as monitor manufacturer, filament or transducer resistance, heat transfer coefficient, thermal mass, filament composition and coefficient of resistance, layout byte, copyright notice, checksum, random data bytes. Porsche U.S. Pat. No. 5,008,843 describes a sensor with EEPROM ID and characteristics data.

BRIEF SUMMARY OF THE INVENTION

The present invention provides a memory chip for use in an oximeter sensor, or an associated adapter or connector circuit. The memory chip allows the storing of patient related data, such as patient trending data or a patient ID, to provide enhanced capabilities for the oximeter sensor. In addition to providing unique data to store in such a memory, the present invention include unique uses of the data stored in such a memory.

DETAILED DESCRIPTION OF THE INVENTION

Figure 1:
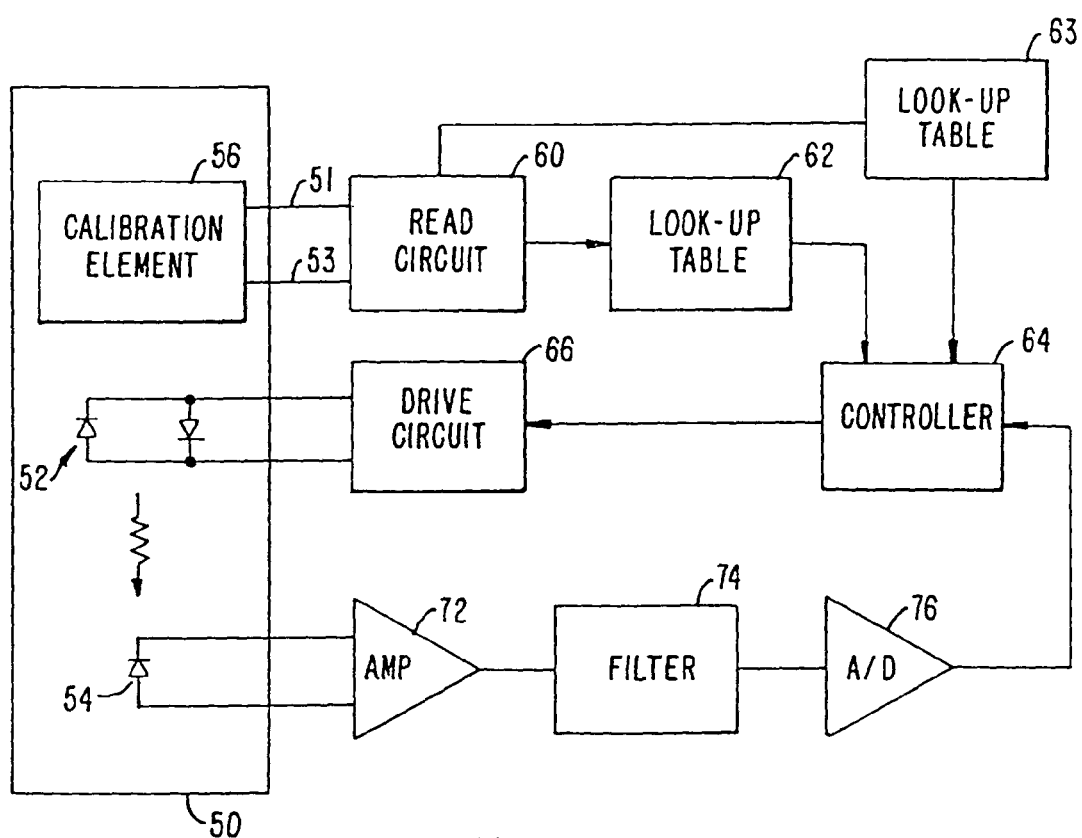
FIG. 1 is a block diagram of a pulse oximeter system in accordance with the present invention.

FIG. 1 is a block diagram of a pulse oximeter system incorporating a calibration memory element 56 according to the invention. In one embodiment, memory element 56 is a two-lead semiconductor digital memory chip. The calibration element is part of the sensor 50 which also includes red and infrared LEDs 52 as in the prior art, along with a detector 54. If desired, LEDs 52 may be replaced with other light emitting elements such as lasers.

The oximeter includes read circuit 60, drive circuit 66, look-up tables 62 and 63, controller 64, amplifier 72, filter 74, and analog-to-digital converter 76. Read circuit 60 is provided for reading multiple coded values across the two leads 51, 53 connected to calibration element 56. One value is provided to a look-up table 62 to determine appropriate wavelength dependent coefficients for the oxygen saturation calculation, as in the prior art. The other value(s) are then provided to another look up table(s) 63 which provides input (e.g., coefficients) to other calculations performed by controller 64. These additional calculations may enhance the performance and/or safety of the system. Controller 64 provides signals to a drive circuit 66, to control the amount of drive current provided to LEDs 52.

As in the prior art, detector 54 is connected through an amplifier 72 and a filter 74 to an A/D converter 76. This forms a feedback path used by controller 64 to adjust the drive current to optimize the intensity range of the signal received. For proper operation the signal must be within the analog range of the circuits employed. The signal should also be well within the range of A/D converter 76. For example, one rule that may be applied is to adjust LED drives and amplifier gains so that both red and IR signals fall between 40% and 80% of full scale reading of converter 76. This requires correct and independent settings for both the red and infrared LEDs.

In an embodiment of the present invention, patient-specific data such as trending data or patient monitoring parameters can be actively stored in the memory of memory chip 56. As the patient and sensor travel from ward-to-ward of the hospital, and consequently plug into different oximeters, the patient-specific data can be read from memory 56 of the patient's dedicated sensor and displayed on a display screen for viewing or used by the oximeter monitor for other purposes. Memory 56 may, for example, be implemented as a random access memory (RAM), a FLASH memory, a programmable read only memory (PROM), an electrically erasable PROM, a similar programmable and/or erasable memory, any kind of erasable memory, a write once memory, or other memory technologies capable of write operations. Examples of patient specific data that can be stored in memory 56 are now discussed.

Patient trending data regarding the history of a patient's blood oxygen saturation ($SPO_2$) level, pulse rate, pulse amplitude, perfusion data, and other patient data over a period of time can be recorded in memory chip 56. The oximeter monitor can continuously or periodically store a patient's current trend data into memory 56 to maintain a historical data for the patient. The patient trend data can be erased from memory 56 each time a sensor is used on a new patient (e.g., each time the oximeter monitor is turned off or when user input to the monitor indicates a new patient). Alternatively, the data encoded into memory 56 can be permanent and non-erasable. Further details of a Method and Circuit for Storing and Providing Historical Physiological Data are discussed in U.S. patent application Ser. No. 09/520,104 to Swedlow et al., filed Mar. 7, 2000, which is incorporated by reference herein in its entirety.

As another example, the lowest and/or highest blood oxygen saturation level, pulse rate, pulse amplitude value, temperature data, blood pressure, perfusion data, or any other patient data during the monitored time may be stored in memory 56 by the oximeter monitor. If desired, the lowest/highest values of these patient parameters over a past specified monitoring time (e.g., 2 hours, 1 day, etc.) may be recorded in memory 56.

Expected ranges for patient parameters (such as pulse rate, pulse amplitude, and blood oxygen saturation level) that are specific to a particular patient may also be recorded in memory 56 by a clinician. This can be a desirable feature, because the expected patient trending data can vary significantly for each patient. The oximeter monitor can compare the expected range for the patient stored in memory 56 with the monitored patient trending data to determine if the patient's pulse and blood oxygen levels are within the expected range for that patient. If the monitored patient parameter varies outside the patient-specific range recorded in memory 56, a warning message may be displayed on the oximeter monitor or alarm signal may be sounded. If desired, any variations in the monitored patient parameters from the expected ranges may be recorded in memory 56 along with a time stamp.

If desired, portions of a patient's medical chart and/or past medical history can be digitally encoded and stored in memory 56 (if sufficient memory space is available) so that this information is maintained with the patient as he is moved around and can be easily accessed and displayed using an oximeter monitor if the patient transferred to a different room or hospital.

The pulse oximeter can keep track of how long a particular patient has been monitored by the pulse oximeter and can periodically store that time interval in memory 56 by checking the elapsed time on a counter. The counter may be a circuit element in the oximeter monitor that is reset each time the oximeter monitor begins to receive data signals from a sensor or each time that the oximeter monitor is turned off. The time period that a patient has been monitored by the oximeter sensor may be displayed on a display screen for viewing.

The pulse oximeter monitor may also include a digital clock that keeps track of the current date and time. The date and time that the oximeter monitor was turned on and the date and time that the oximeter monitor was turned off may be encoded into the sensor in memory 56. When the oximeter monitor is turned back on again, the monitor can display the date and time that it was last turned on and off. It may be desirable for medical personnel to know the last time that patient's vital signs were monitored by the oximeter.

The oximeter monitor instrument may also write the alarm limits used with a particular patient into memory chip 56. Alarm limits are values that represent maximum or minimum values of patient trending data tracked by the oximeter (such as blood oxygen saturation, pulse rate, pulse amplitude, etc.) that will trigger an alarm, because they are considered to be dangerous levels. The alarm limit values may be encoded in memory 56 by the manufacturer or by a clinician through the oximeter monitor prior to operation.

The oximeter monitor periodically checks the patient's monitored trending data against the alarm limit values. When one of the monitored patient parameters reaches the alarm limit value stored in memory 56, the oximeter monitor triggers an alarm which alerts medical personnel that a problem may exist. The present invention also allows patient-specific alarm values to be set by medical personnel through the oximeter and stored in memory 56 so that as the patient moves from monitor-to-monitor (while the sensor stays with the patient), the appropriate alarm limits need not be reset each time on the new monitor. Instead, the alarm limits only need to be programmed once, or at a later time, whenever the clinician adjusts alarm limits.

One of more of the patient trending data including blood oxygen saturation, pulse rate, and pulse amplitude can be written to memory 56 along with a time of occurrence whenever an alarm threshold is crossed. Additional information, such as the readings for a predetermined time prior to an alarm occurrence can also be stored, and/or periodic values during the alarm breach can also be stored in memory 56.

Currently sensors are placed on patients at one hospital site and stay with the patient from hospital site-to-site. It would therefore be desirable to have a patient identification code (patient ID)-such as a unique number carried along in the sensor so that the record keeping, which occurs at each site, can link the recorded information with the patient. Without a patient ID stored in the sensor itself, the tracking has to be done manually. This method is prone to mistakes and increases the labor involved in managing the patient.

Thus, in a further embodiment of the present invention the oximeter monitor can store a patient ID in memory 56 of sensor 50. The oximeter has an input device such as a keyboard, touch screen, or scanner that allows a patient ID to be entered and reentered into the oximeter so that it can be stored in sensor memory 56. With patient trending information being stored in memory 56 of the sensor as discussed above, it is also desirable to have the patient ID stored in memory 56 so that as the patient goes from hospital location to location, the new location's staff can verify that old trending information stored in memory 56 was indeed obtained from that particular patient. Medical personnel can check that the patient ID stored in sensor 50 matches the patient ID on the patient's chart and other paper documentation to verify that these medical records correspond to the correct patient. If desired, the oximeter sensor can be interfaced with a hospital computer network that maintains a database of patient ID numbers to verify the identify of the patient and to obtain medical records and other information for the patient stored on hospital databases. The patient ID stored in memory 56 provides assurance that any data read from memory 56 of the sensor is correlated with the patient they are receiving.

The pulse amplitude of the measured photoplethysmogram is an indirect measure of blood perfusion (flow) in the local tissue, changes in blood pressure, vascular tone, vasoconstriction or dilation, for example, all have an effect on the pulsatile signal strength observed with a pulse oximeter.

The measured modulation, or other measurement of perfusion, can be stored in memory 56 for patient trending purposes. The oximeter can compare current modulation and perfusion data with older data from memory 56 to determine patient trends over time. The patient's pulse amplitude deteriorating over time may reflect a serious condition that demands attention. Therefore, it is desirable to store and monitor changes in a patient's perfusion over time. Also, a maximum or minimum perfusion limit may be stored in memory 56 that represents the maximum or minimum value that the patient's measured perfusion can reach before the sensor needs to be moved, repositioned, or adjusted in some other way. The oximeter can trigger a warning signal or light when a perfusion limit has been reached or a significant change has occurred.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiments disclosed, but that the invention will include all embodiments and equivalents falling within the scope of the claims.

What is claimed is:

1. A method of operation of an oximeter system, comprising:
    directing light at a patient from a light emitter of an oximeter sensor;
    detecting the light with a light receptor of the oximeter sensor;
    transmitting a patient-type data alarm limit from a memory of the oximeter sensor to an oximeter monitor, wherein the patient-type data alarm limit is based on a type of patient for which the sensor is adapted; and
    comparing the patient-type data alarm limit with a monitored patient parameter.

2. The method of claim 1, wherein the patient-type data alarm limit includes a range of expected patient parameters for a particular type of patient.

3. The method of claim 1, comprising sending an alarm signal when a value of the monitored patient parameter crosses the patient-type data alarm limit.

4. A method of manufacturing an oximeter system, comprising:
    providing a light emitting element configured to direct light at a patient;
    providing a light receptor configured to detect the light;
    providing a memory in the sensor, the memory storing a patient-type data alarm limit, wherein the patient-type data alarm limit is based on a type of patient for which the sensor is adapted; and
    providing a pulse oximeter monitor configured to receive the patient-type data alarm limit from the memory of the sensor and to compare the patient-type data alarm limit with a monitored patient parameter.

5. The method of claim 4, comprising providing a communication device in the sensor, the device configured to transmit the patient-type data alarm limit to the pulse oximeter monitor for use in an algorithm for comparing the patient-type data alarm limit with the monitored patient parameter.

6. A method of operation of an oximeter system, comprising:
    directing light at a patient from a light emitter of an oximeter sensor;
    detecting the light with a light receptor of the oximeter sensor;
    transmitting a patient-type data alarm limit from a memory of the oximeter sensor to an oximeter monitor, wherein the patient-type data alarm limit is based on a type of patient for which the sensor is adapted;
    comparing the patient-type data alarm limit with a monitored patient parameter; and
    receiving an updated patient-type data alarm limit and replacing the patient-type data alarm limit in the memory with the updated patient-type data alarm limit.

7. A method of operation of an oximeter monitor, comprising:
    receiving, at the oximeter monitor, a patient-type data alarm limit from a memory of an oximeter sensor, wherein the patient-type data alarm limit is based on a type of patient for which the sensor is adapted; and
    comparing the patient-type data alarm limit with a monitored patient parameter with the oximeter monitor.

* * * * *